United States Patent [19]

Rogers et al.

[11] Patent Number: 5,252,711
[45] Date of Patent: Oct. 12, 1993

[54] MONOCLONAL ANTIBODIES USEFUL IN DEODORIZING SKIN AND ANTIBODY FRAGMENTS THEREOF

[75] Inventors: Brian Rogers, Mt. Airy, Md.; Anne Maczulak, Arlington, Va.

[73] Assignee: The Gillette Company, Boston, Mass.

[21] Appl. No.: 766,521

[22] Filed: Sep. 27, 1991

Related U.S. Application Data

[62] Division of Ser. No. 360,154, Jun. 1, 1989, Pat. No. 5,069,896.

[51] Int. Cl.$^5$ .............. A61K 7/32; A61K 39/395; C07K 15/28; C12N 5/12
[52] U.S. Cl. ............... 530/388.2; 530/388.4; 530/388.1; 424/87
[58] Field of Search ............ 424/87; 530/388.1, 388.2, 530/388.4

[56] References Cited

U.S. PATENT DOCUMENTS

| | | | |
|---|---|---|---|
| 3,128,230 | 4/1964 | Heinbach | 167/78 |
| 3,376,198 | 4/1968 | Petersen et al. | 167/78 |
| 3,907,987 | 9/1975 | Wilson | 424/92 |
| 4,271,145 | 6/1981 | Wands et al. | 424/85 |
| 4,284,623 | 8/1981 | Beck | 424/85 |
| 4,361,509 | 11/1982 | Zimmerman et al. | 424/85 |
| 4,364,934 | 12/1982 | Kung et al. | 424/85 |
| 4,423,147 | 12/1983 | Secher et al. | 435/68 |
| 4,430,437 | 2/1984 | Hampar et al. | 436/548 |
| 4,474,893 | 10/1984 | Reading | 436/547 |

OTHER PUBLICATIONS

Carrasco et al, Monoclonal Ab . . . Studies, 1984, Biochemistry 23:3681-3687.

Korting et al, Microbial Flora . . . skin., 1988 Hantartz 39:564–568 (Abstract only).

Goding, Monoclonal Ab: Principles & Practice 1986 pp. 59-77.

Herzlinger et al. *Biochemistry*, vol. 23, 1984, "Monoclonal Antibodies Against the Iac Carrier Protein from *Escherichia Coli*. 2. Binding Studies with Membrane Vesicles and Proteoliposomes Reconstituted with Purified Iac Carrier Protein", pp. 3688-3693.

T. J. Kipps et al. *Handbook of Experimental Immunology*, vol. 4, 1986, "Schemata for the Production of Monoclonal Antibody-producing Hybridomas", pp. 108.1-108.9.

Fan et al. *Applied and Environmental Microbiology*, vol. 54, No. 12, Dec. 1988, "Production and characterization of a Monoclonal Antibody Cross-Reactive with Most Group A Trichothecenes", pp. 2959-2963.

Ingham et al. *British Journal of Dermatology*, vol. 116, 1987, "Antibodies to P. acnes and P. acnes exocellular enzymes in the normal population at various ages in patients with acne vulgaris", pp. 805-812.

*Primary Examiner*—David L. Lacey
*Assistant Examiner*—F. C. Eisenschenk
*Attorney, Agent, or Firm*—Burns, Doane, Swecker & Mathis

[57] ABSTRACT

The present invention is concerned with a monoclonal antibody or antigen-binding fragment of a monoclonal antibody produced by a hybridoma formed by fusion of cells from mouse myeloma cells and spleen cells wherein the monoclonal antibody or fragment thereof reacts with the carrier or transfer protein of a bacterial cell. The bacterial cell may be coryneform bacteria or bacteria of the genus Staphylococcus.

10 Claims, No Drawings

MONOCLONAL ANTIBODIES USEFUL IN DEODORIZING SKIN AND ANTIBODY FRAGMENTS THEREOF

This application is a divisional application of 07/360,154, filed Jun. 1, 1989 now U.S. Pat. No. 5,069,896.

BACKGROUND OF THE INVENTION

The present invention relates to a monoclonal antibody (McAb) produced by a hybridoma cell line. The McAb has specificity to transport proteins of bacterial cells and results in the inhibition of the formation of axillary malodor.

Human body odor is caused by bacteria that normally inhabit the skin. These bacteria may rely on some components of perspiration which serve as nutrients for the growth of the bacteria. Based on the amount of perspiration formed, the axillary area is one of the primary areas of concentration of bacteria on the human body. The secretions in perspiration may serve as nutrients for bacterial growth or as precursor compounds for bacterial metabolic pathways leading to malodor formation.

Various approaches have been taken to solve the problem of axillary malodor. One approach has been the use of antiperspirants. Antiperspirants may prevent the formation of odor by inhibiting perspiration, thereby depriving the bacterial metabolic pathways leading to malodor formation of the necessary substrates, or by exerting a direct antimicrobial effect on the bacteria present in the axilla. Another approach has been the use of deodorants which attempt to mask the odor produced. A third approach has been the use of germicides which kill or inhibit the reproduction of bacteria.

A number of prior art publications have suggested using antibodies which react with and thereby kill certain species of bacteria. It is known that the body produces different types of antibodies which function in different environments.

There are five known classes of antibodies including IgG, IgM, IgA, IgE and IgD. Four of the antibody classes, namely IgG, IgM, IgE and IgD, are referred to as humoral antibodies because they naturally occur in the blood and function in those parts of the body that come in direct or indirect contact with the blood. Humoral antibodies can also be found in the tissue fluids of the body. The tissue fluids receive the humoral antibodies of the blood by diffusion of the antibodies from the blood into the surrounding tissue fluids by a process known as transudation. The IgA antibody is referred to as a secretory antibody because it is found in the fluids secreted by the epithelial cells which line the surfaces of hollow body organs. The IgA antibody functions as a barrier by protecting the surface of the gastrointestinal tract from infection by bacteria and viruses and by preventing the absorption of toxins and poisons by the gastrointestinal epithelium.

Milk is a logical choice for the production of a deodorant antibody since it contains the same classes of antibody found in secretions of mammalian sebaceous glands. The only exception is the milk of dairy cows contains principally IgG antibody.

An example of antibody-containing milk is disclosed in U.S. Pat. No. 3,376,198. The antibody-containing milk is effective in providing antibodies which counteract a number of different bacteria and viruses depending upon the antigen administered to a cow. U.S. Pat. No. 3,128,230 also illustrates an antibody-containing milk generated more specifically against the bacterial species *Escherichia coli*, *Streptococcus viridans* and *Diplococcus pneumoniae*. U.S. Pat. No. 3,907,987 discloses an antibody-containing milk which is effective against microorganisms responsible for enteric diseases.

European Patent Application No. 0,127,712 suggests using a non-specific antibody preparation for milk directed against a large number of bacterial species associated with human skin as a deodorant. This antibody was prepared without a specific understanding of the malodor-causing bacterial species which inhabit human skin.

Antibodies can be developed against specific bacterial species or even specific enzyme systems within a bacterial cell (*Brit J. Dermatol.* 116:805–812, 1978). This specificity can be achieved by developing a McAb directed against a particular bacterial system associated with the malodor-forming pathway.

The prior art has not heretofore suggested or recognized the possibility of producing a McAb to the cellular transport protein of bacteria which is responsible for delivering the malodor precursor compound into the bacterial cell.

SUMMARY OF THE INVENTION

The present invention is a method of preventing the formation of axillary malodor by applying to a human a composition comprising antibodies directed against the transport protein of bacterial cells involved in the production of malodor.

Contrary to any prior art processes heretofore recognized, by inhibiting the transport of selected compounds into the bacterial cell, malodor would be prevented, leaving the bacterial cell intact and viable.

DETAILED DESCRIPTION OF THE INVENTION

The present invention includes the discovery that malodor can be decreased or eliminated using the McAb produced by a hybridoma cell line wherein the antibody has specificity against a transport protein used to transfer certain compounds into the cell.

The skin areas producing the greatest perspiration also have the greatest bacterial populations However, not all of the bacteria which are present on the skin cause malodor. The malodor-causing bacteria are those which can absorb and convert specific precursor compounds into one or more malodorous compounds using their cellular metabolism. For instance, species of bacteria which produce malodor from secretions in perspiration include Staphylococcus naemolyticus and the coryneform bacteria.

The identification of bacteria as malodor-producers involves a screening method for determining the presence or absence of a volatile malodor compound. One such method involves a) adding 100 microliters of a malodor-producing cell suspension to a vial which contains concentrated and dried malodor precursor compound, b) incubating the mixture for approximately 30 minutes at 37° C., c) adding 200 microliters of chloroform then capping the vials, d) allowing the vials to stand for at least 15 minutes at room temperature, e) removing about 50 microliters of the chloroform layer and applying the chloroform layer to a strip of bibulous paper, and f) sniffing the paper for the presence of malodor after the chloroform has evaporated.

The malodor-producing bacteria are unique in that they possess an intracellular malodor-forming enzyme. It is a metalloenzyme which acts as an amino acid lyase and its activity depends upon the presence of pyridoxal phosphate as a co-factor. Upon storage at 4° C., these bacteria lose the ability to produce malodor; however, after harvest and lysis of the cells, an active malodor-forming enzyme can be recovered. While not wishing to be bound by any particular theory, this suggests that a labile transport system for the malodor precursor compound is required for the transfer of precursor compounds into the cell whereupon it serves as a substrate for the malodor-forming enzyme.

Ions, sugars and amino acids are transported into bacteria using either group translocation, facilitated diffusion, simple diffusion or active transport. Amino acids are usually transported by active transport mechanisms which require the expenditure of cellular energy to transport a compound up a chemical gradient. It has been shown that structurally related amino acids use the same active transport carrier. There is evidence that the malodor precursor compound, a sulfur-containing amino acid, uses the same active transport carrier as L-cysteine. A McAb specific for the precursor carrier protein blocks the formation of malodor by preventing precursor uptake by the cell.

Recently, it has been demonstrated that a McAb can be produced in mice to react with an extracellular toxin produced by the fungus Fusarium as noted in *Appl. Environ. Microbiol.*, 54:2959-2963, 1988. The steps employed in McAb development against a variety of specific target substrates have some general procedures in common. The first step involves the development of a specific antigenic material which will induce an immunologic response from antibody-generating cells in vivo. These immunocytes are then recovered and fused with an appropriate immortalizing cell line such as mouse myeloma cells. Subsequent to this fusion, the resulting hybridoma cells are grown under conditions which allow for production of the specific desired antibody. Hybridoma colonies are recovered and screened for this ability to produce the antibody, then the most enzyme-linked immunosorbent assay-positive hybridoma lines are cloned. Once these lines are cloned, known methods can be employed to maximize the production of the McAb.

The McAb-containing material can be applied to the skin in a variety of ways to accomplish the intended object of deodorizing the skin. The McAb-containing substance itself may be applied directly to the skin, preferably the axilla, or it may be applied as the active ingredient in a composition comprising the McAb and an inert vehicle. Suitable vehicles include gels, liquid sprays (pumps and aerosols), creams, liquids, lotions, oils, ointments, solid stick applicators and the like. The most preferred compositions for application to the underarms are solid sticks, roll-on emulsions, creams and lotions.

In all formulations, it is important that the McAb be compatible with the ingredients of the topical skin vehicle, that is, the McAb must maintain its viability in the formulations selected. For example, nothing that may denature the McAb-containing material should be present in the formulation. In general, there should be less than 10% alcohol and less than 1% denaturing detergents The preferred propellant in the formulation is $CO_2:N_2$.

Any of the ingredients commonly employed in the manufacture of compositions applied topically to the skin, and which have no adverse effect on the active ingredient, may be used. The use of an FAb, the antigen-binding fragment of the McAb, may be more stable than the entire McAb and thus more efficacious in these compositions.

There are a variety of methods known in the art for producing FAb. Methods for producing FAb fragments directly from cell culture supernatants include digestion of the antibody with pepsin at pH 3.5 to 4.0. The pepsin at a concentration of 25 ug/ml in 0.1M citrate buffer, pH 3.5, can digest IgG antibody incorporated at 1 to 2 mg/ml. Similar digestion systems using trypsin having been shown to produce FAb fragments from IgM antibodies in the presence of a reducing agent. Purification of FAb fragments is completed by dialysis followed by column chromatography. Antigen-binding capacity has been found to remain associated with both heavy-chain and light-chain binding sites associated with the resultant FAb fragments.

In order to further illustrate the present invention and the advantages thereof, the following specific examples are given, it being understood that these examples are intended only to be illustrative without serving as a limitation on the scope of the present invention.

EXAMPLE 1

Preparation of an Antigen for the Development of an Anti-Malodor Antibody

Malodor-producing Staphylococcus and coryneform bacteria were isolated from the axillae of several individuals by washing the axilla with 2.0 ml of sterile saline, diluting this wash serially in saline, and plating the cell suspension on letheen agar plates. The inoculated plates were incubated at 37° C. for 24 hours followed by an additional incubation at 25° C. for 24 hours. Large yellow colonies were examined microscopically and biochemically and were typed as *Staphylococcus haemolyticus*, which when screened for the ability to produce malodor as described above were found to be malodor-positive. Similarly, small translucent colonies were typed as bacteria of the coryneform group and were also malodor-positive.

A 100 ml culture of the Staphylococcus was grown in Tryptic Soy Broth, harvested, and re-suspended in 50 mM phosphate buffer, pH 6.8. The cells were lysed using a sonication method, and cell wall and cell membrane fragments were separated from the soluble materials by centrifugation.

The cell wall/membrane fraction was diluted to 38.1 micrograms protein/ml in 0.1M carbonate buffer, pH 9.6. This preparation was used as the antigen in an immunization schedule in which Balb/c mice were challenged and boosted over a 12-week period.

EXAMPLE 2

Immunization of Mice for Raising an Anti-Malodor Antibody

In vivo immunization of Balb/c mice was conducted using the antigen described above. Each mouse received 100 micrograms of antigen per subcutaneous inoculation. Sera collection included one pre-inoculation bleed and three test bleeds. Each test bleed was performed 10 days after a boost inoculation. The pre-bleed and three test bleeds were individually screened for potential anti-malodor antibody activity by treating the washed-cell suspension, containing on the order of $10^9$ cells/ml, with an equal volume of test serum. Each mixture was incubated for one hour at room temperature then screened for the production of the volatile malodor compound according to the method described above.

Activity of the sera was simultaneously screened against the specific antigenic preparation by ELISA. The mouse having the highest titer of anti-Staphylococcus cell wall/membrane antibody was sacrificed for subsequent recovery of antibody-producing splenocytes. It was noted that the serum from this mouse also had anti-malodor antibody activity against both Staphylococcus and coryneform bacteria as determined by the malodor assay.

EXAMPLE 3

Development of a Hybridoma Cell Line for the Production of an Anti-Transport Monoclonal Antibody The mouse having the highest serum titer of desired antibody, as determined by the ELISA and malodor assays, was sacrificed and the spleen removed under aseptic conditions. A suspension of splenocytes of $2.2 \times 10^7$ cells/ml was prepared. A suspension of cells of $6.2 \times 10^6$/ml from a myeloma cell line was also prepared. The splenocytes and myeloma cells were combined in a ratio (spleen:myeloma) of 4:1. The cells were treated and recovered by centrifugation in Iscove's Modified Dulbecco's Medium (IMDM) with hypoxanthine-adenine-thymidine (HAT) in the presence of 50% (w/v) polyethylene glycol. Following this fusion treatment, the cells were recovered by centrifugation and resuspended in 33.0 ml of IMDM with HAT for every $1.6 \times 10^8$ cells. The suspension was dispersed dropwise into a total of 600 wells in microwell plates and incubated for seven days at 37° C. in a dry $CO_2$ (5%) incubator. The wells which had 30-50% confluent growth of hybridoma cells were screened by ELISA and by the malodor assay. Each hybridoma line (corresponding to a well) which was associated with both a positive ELISA response and a positive activity against malodor production was chosen for subsequent cloning.

The desired hybrid cells were diluted serially with IMDM to obtain a final concentration of 100 cells in 30 ml IMDM and 10% fetal bovine serum. Spleen cells were added to give a concentration of $3-5 \times 10^6$ feeder cells/ml. The suspension was dispersed into microwell plates and incubated at 37° C. in a $CO_2$ (5%) incubator. Following growth, the clones were again assayed for a positive ELISA response and activity against malodor production. Lines having the highest titers were chosen for a second cloning and tested again.

All hybridoma cell lines having been cloned at least one time and showing significant activity by ELISA and malodor screens were preserved by controlled rate freezing in IMDM. The cell lines were stored in cryopreservation tubes in liquid nitrogen.

EXAMPLE 4

In Vitro Production of Anti-Transport Monoclonal Antibody and Quantitation of its Activity Individual hybridoma cell lines were recovered from frozen stocks and expanded in WRC 935 serum-free basal medium manufactured by W.R. Grace & Co. supplemented with insulin, transferrin and albumin. At confluency, cells were passed by a scraping technique and were transferred to new flasks containing fresh medium. The antibody-containing medium was collected semi-weekly and the cells were introduced to fresh medium. The collected medium was stored at 4° C. until procedures for the quantitation of the antibody were performed.

The collections of antibody-containing media were pooled then concentrated to a 50 ml volume using an Amicon stirring ultrafiltration cell and membrane with a molecular weight cut-off of 30,000 daltons. The antibody-containing fraction was further concentrated by lyophilization. Lyophilized product was dissolved in distilled, deionized water. Quantitation was performed using both the ELISA and malodor assay techniques. Application of the anti-transport McAb to an SDS-polyacrylamide electrophoresis gel followed by a Western blot indicated that the McAb reacts with a single protein from the Staphylococcus cell wall/membrane fraction having a molecular weight of 50,000 daltons.

In vitro malodor assays on McAb-treated malodor-producing Staphylococcus cells showed that between 7 and 35 nanograms of the McAb were required to block precursor transport in an order of $10^8$ bacteria. This exceeds the concentration of malodor-producing cells present in the axilla. Therefore, it is expected that the McAb is an effective anti-transport agent at low concentrations.

A human malodor neutralization study was conducted and the McAb formulations were found to be effective.

EXAMPLE 5

A deodorant stick formulation may be prepared as follows:

| Compound Name | % |
| --- | --- |
| Methyl gluceth-20 distearate | 10 |
| Propylene Glycol | 72 |
| Sodium stearate C-1 | 6 |
| Fragrance | 0.1 |
| 0.2%, Active ingredient in water, neutral pH | 11.9 |

EXAMPLE 6

A deodorant roll-on emulsion may be prepared as follows:

| Compound Name | % |
| --- | --- |
| Hydrogenated palm oil glycerides and sodium cetyl sulfate (Lamecreme CSM) | 1 |
| Steareth-7 (Lamecreme SA-7) | 1 |
| Octyldodecanol | 4 |
| Glyceryl laurate (Monomuls 90-1 12) | 2 |
| Octyl palmitate | 4 |
| Dimethicone | 1 |
| Propylparaben | 0.1 |
| Methylparaben | 0.2 |
| Imidazolidinyl urea | 0.3 |
| Glycerin | 5 |
| Allantoin | 0.5 |
| PEG-35 lanolin (Lamecerin 50-80) | 0.5 |
| Fragrance | 0.3 |
| 0.3%, Active ingredient in water, neutral pH | 79.6 |

EXAMPLE 7

An antiperspirant and deodorant roll-on emulsion may be prepared as follows:

| Compound Name | % |
| --- | --- |
| PPG-15 stearyl ether (Arlamol E) | 4 |
| Steareth-21 (Brij 721) | 0.6 |
| Steareth-2 | 2.6 |
| Aluminumzirconium pentachlorohydrate, 10:1, 25% solution | 32 |
| Fragrance | 0.1 |
| 0.4%, Active ingredient in water, neutral pH | 60.7 |

EXAMPLE 8

An antiperspirant and deodorant stick formulation may be prepared as follows:

| Compound Name | % |
| --- | --- |
| Aluminum chlorohydrate (Wickenol CPS-331 | 16 |
| Polypropylene glycol | 30 |
| Sorbitol, 70% | 3 |
| Sodium stearate C-1 | 5 |
| Sodium ceteth-13 carboxylate (Sandopan KST) | 3 |
| Stearyl alcohol Aldol 62 Flake) | 1 |
| Cyclomethicone (Volatile Silicon 7158) | 15 |
| Fragrance | 0.1 |
| 0.1%, Active ingredient in water neutral pH | 26.9 |

EXAMPLE 9

An antiperspirant and deodorant cream formulation may be prepared as follows:

| Compound Name | % |
| --- | --- |
| Condensate of ethylene oxide with a hydrophobic base formed by condensing propylene oxide with propylene glycol (Pluronic F-68) | 5 |
| Cetyl trimethyl ammonium bromide | 0.5 |
| Cetyl alcohol | 1 |
| Glyceryl monostearate | 13 |
| Spermaceti wax | 4 |
| Glycerine | 3 |
| Polyoxyalkylene propylene glycol monostearate | 0.5 |
| Polyoxyalkylene stearate | 0.5 |
| Ethanol | 2 |
| Fragrance | 0.1 |
| 0.2%, Active ingredient in water, neutral pH | 70.4 |

EXAMPLE 10

An antiperspirant and deodorant lotion formulation may be prepared as follows:

| Compound Name | % |
| --- | --- |
| Condensate of ethylene oxide with a hydrophobic base formed by condensing propylene oxide with propylene glycol (Pluronic F-68) | 10 |
| 8-Hydroxyquinoline sulfate | 0.8 |
| Ethanol | 2 |
| Veegum | 3.5 |
| Mineral oil | 6 |
| Stearyl alcohol | 1.5 |
| Polyoxyalkylene propylene glycol monostearate | 0.8 |

| Compound Name | % |
| --- | --- |
| Polyoxyalkylene stearate | 0.8 |
| Fragrance | 0.1 |
| 0.2%, Active ingredient in water, neutral pH | 74.5 |

EXAMPLE 11

An aerosol deodorant formulation may be prepared as follows:

| Compound Name | % |
| --- | --- |
| Dioctyladipate | 10 |
| Quaternium 18 hectorite | 1 |
| Dioctyl succinate | 10 |
| SDA 40 ethanol, anhydrous | 1 |
| Wheat germ glycerides | 0.1 |
| Fragrance | 0.1 |
| 0.2%, Active ingredient in water, neutral pH | 1 |
| $CO_2:N_2$ Propellent | 76.8 |

EXAMPLE 12

An aerosol antiperspirant and deodorant formulation may be prepared as follows:

| Compound Name | % |
| --- | --- |
| Isopropyl myristate | 13.4 |
| Aluminum chlorhydrate | 10 |
| Quaternium-18 hectorite (Bentone 38) | 0.8 |
| SDA 40 anhydrous | 0.8 |
| Fragrance | 0.1 |
| 0.2%, Active ingredient in water, neutral pH | 1 |
| $CO_2:N_2$ Propellent | 26.9 |

What is claimed is:

1. A murine monoclonal antibody produced by a hybridoma formed by fusion of cells from mouse myeloma cells and spleen cells, wherein said antibody specifically binds with the 50,000 dalton carrier or transfer proteins of a malodor producing bacterial cell to prevent malodor formation, said bacterial cell being a coryneform bacteria or of the genus Staphylococcus.

2. The monoclonal antibody according to claim 1, wherein said antibody reacts with the carrier or transfer protein to block the uptake of precursor compounds which produce malodor into the bacterial cell.

3. The monoclonal antibody according to claim 1 wherein the bacterial cell is of the genus Staphylococcus.

4. The monoclonal antibody according to claim 2 wherein the bacterial cells is coryneform bacteria.

5. The monoclonal antibody according to claim 1, wherein said monoclonal antibody is the IgG type.

6. The monoclonal antibody according to claim 1 wherein said monoclonal antibody is the IgM type.

7. The monoclonal antibody according to claim 1 wherein the carrier or transport protein is found in the cell wall of malodor-producing skin bacteria.

8. An antigen-binding fragment of a monoclonal antibody according to claim 1.

9. The fragment according to claim 8 wherein the bacteria are of the genus Staphylococcus.

10. The fragment according to claim 8 wherein the bacterial are coryneform bacteria.

* * * * *

UNITED STATES PATENT AND TRADEMARK OFFICE
CERTIFICATE OF CORRECTION

PATENT NO. : 5,252,711
DATED : October 12, 1993
INVENTOR(S) : Brian ROGERS and Anne MACZULAK It is certified that error appears in the above-indentified patent and that said Letters Patent is hereby corrected as shown below:

Column 2, line 46, after "bacterial", delete "populations", and
    insert --populations.--;
        line 53, delete "naemolyticus" and insert --haemolyticus--.

Column 3, line 67, delete "gents" and insert --gents.--.

Signed and Sealed this

Twenty-second Day of February, 1994

Attest:

BRUCE LEHMAN

Attesting Officer     Commissioner of Patents and Trademarks